United States Patent
Tanase et al.

(10) Patent No.: US 8,804,120 B2
(45) Date of Patent: Aug. 12, 2014

(54) FINE PARTICLE ANALYZING APPARATUS AND FINE PARTICLE ANALYZING METHOD

(75) Inventors: Hironobu Tanase, Tokyo (JP); Mitsuru Toishi, Kanagawa (JP)

(73) Assignee: Sony Corporation, Tokyo (JP)

( * ) Notice: Subject to any disclaimer, the term of this patent is extended or adjusted under 35 U.S.C. 154(b) by 127 days.

(21) Appl. No.: 13/417,400

(22) Filed: Mar. 12, 2012

(65) Prior Publication Data

US 2012/0250018 A1 Oct. 4, 2012

(30) Foreign Application Priority Data

Mar. 31, 2011 (JP) .................................. 2011-080621

(51) Int. Cl.
*G01N 21/49* (2006.01)
*G01N 15/14* (2006.01)

(52) U.S. Cl.
CPC .................................. *G01N 15/1434* (2013.01)
USPC .............................. 356/338; 356/73; 250/574

(58) Field of Classification Search
CPC .............. G01N 15/1434; G01N 15/04; G01N 15/1404; G01N 15/1459; G01N 15/1463; G01N 15/1429; G01N 15/1425; G01N 21/17; G01N 2015/1486; G01N 2015/1493; G01N 2021/4707
USPC .............. 356/73, 335–343; 250/459.1, 458.1; 385/28, 39; 372/38.02, 38.1, 38.04, 372/38.07
See application file for complete search history.

(56) References Cited

U.S. PATENT DOCUMENTS

| | | | | |
|---|---|---|---|---|
| 5,530,551 A | * | 6/1996 | Cantrall et al. | 356/394 |
| 5,684,642 A | * | 11/1997 | Zumoto et al. | 359/740 |
| 6,778,570 B2 | * | 8/2004 | Tanase | 372/38.02 |
| 7,120,173 B2 | * | 10/2006 | Roques et al. | 372/3 |
| 7,477,383 B2 | * | 1/2009 | Furman et al. | 356/338 |
| 7,755,760 B2 | * | 7/2010 | Nakajima et al. | 356/338 |
| 8,350,232 B2 | * | 1/2013 | Fukumoto et al. | 250/459.1 |
| 8,384,045 B2 | * | 2/2013 | Takasaki et al. | 250/459.1 |
| 2004/0141176 A1 | * | 7/2004 | Snelling et al. | 356/335 |
| 2011/0293897 A1 | * | 12/2011 | Kawashima | 428/195.1 |

FOREIGN PATENT DOCUMENTS

| | | |
|---|---|---|
| JP | 05-232012 | 9/1993 |
| JP | 09-178645 | 7/1997 |
| JP | 2005-172465 | 6/2005 |
| JP | 2009-053020 | 3/2009 |

* cited by examiner

*Primary Examiner* — Hoa Pham
(74) *Attorney, Agent, or Firm* — K&L Gates LLP

(57) ABSTRACT

A fine particle analyzing apparatus includes a light irradiation unit configured to irradiate a fine particle that flows in a flow path with a laser beam, and a detection unit configured to detect light emitted from the fine particle that is irradiated with the laser beam. In the fine particle analyzing apparatus, the light irradiation unit includes at least a light source that is composed of a semiconductor laser, an optical fiber that converts a beam pattern of the laser beam generated from the light source into a top-hat type beam pattern, and a light source driving control unit configured to supply driving current, which is obtained by superimposing high-frequency current on direct current, to the light source.

4 Claims, 5 Drawing Sheets

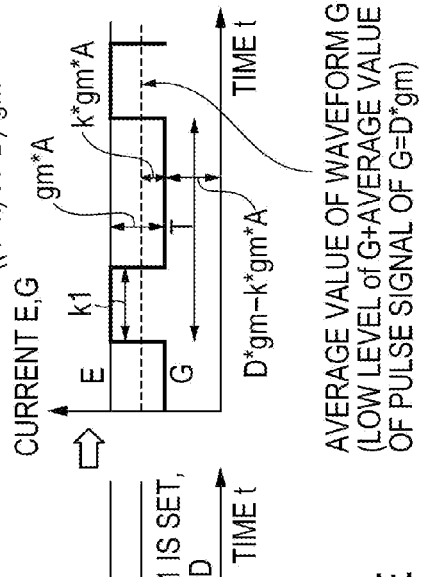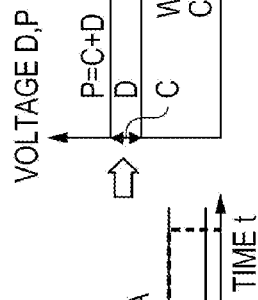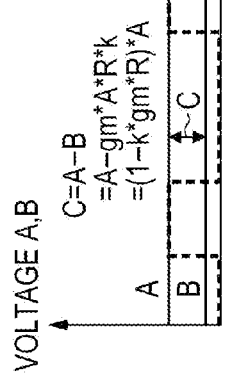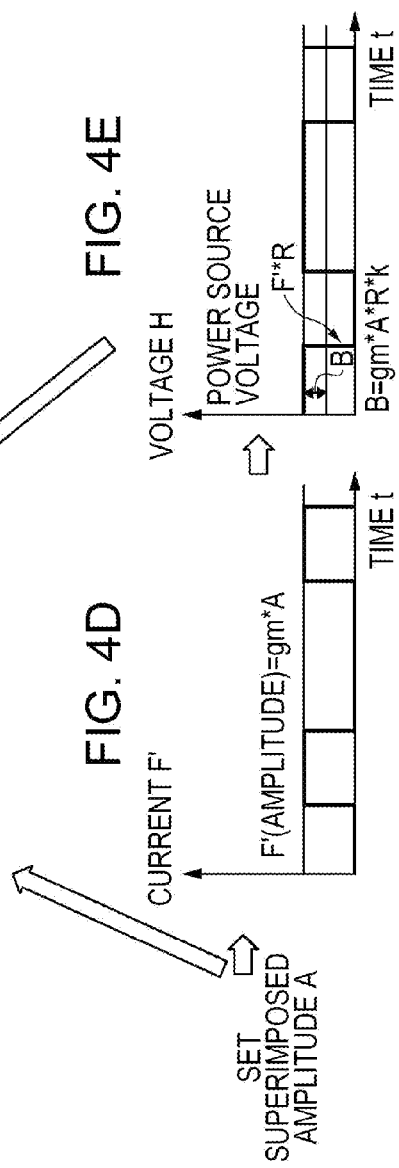

FINE PARTICLE ANALYZING APPARATUS AND FINE PARTICLE ANALYZING METHOD

CROSS REFERENCES TO RELATED APPLICATIONS

The present application claims priority to Japanese Priority Patent Application JP 2011-080621 filed in the Japan Patent Office on Mar. 31, 2011, the entire content of which is hereby incorporated by reference.

BACKGROUND

The present application relates to a fine particle analyzing apparatus and a fine particle analyzing method by which a sample such as a fine particle is optically detected. In particular, the present application relates to a fine particle analyzing apparatus and a fine particle analyzing method in which semiconductor laser is used as a light source.

Commonly, when physiologically-related fine particles such as cells, microorganisms, and liposome are identified, an optical measuring method using flow cytometry (flow cytometer) is employed (For example, Supervised by H. Nakauchi, "Cell Engineering Additional Volume, Experimental Protocol Series, Freely Flow Cytometry", Second Edition, Shujunsha Co., Ltd., published on Aug. 31, 2006). Flow cytometry is a method in which fine particles flowing in a flow path in a line are irradiated with laser beams having a specific wavelength and thus fluorescence or scattering light emitted from each of the fine particles is detected so as to singly identify the plurality of fine particles.

Specifically, a laminar flow is formed by sample liquid containing fine particles which are measurement objects and sheath liquid which flows around the sample liquid, so as to line up the plurality of fine particles contained in the sample liquid, in the flow path. When laser beams are radiated to the flow path in such state, the fine particles pass transversely across the laser beams one by one. At this time, fluorescence and/or scattering light which are/is excited by the laser beams and emitted from each of the fine particles are/is detected with an optical detector such as a charge coupled device (CCD) and a photo-multiplier tube (PMT). Then, the light detected by the optical detector is converted into an electric signal to be digitized and statistical analysis is performed so as to determine a type, a size, a structure, and the like of each of the fine particles.

Meanwhile, in order to quantitatively and stably analyze a sample in the flow cytometry described above, it is preferable to constantly maintain the light amount of excitation light (laser beam) radiated to the sample steady. However, a beam spot of excitation light (laser beam) is commonly small such as about several dozen μm, and variation in power density occurs in a three-dimensional direction (an optical axis depth direction and a direction orthogonal to the optical axis) in a beam spot.

Therefore, in related art, a fine particle analyzing apparatus that controls laser driving so as to reduce noise derived from a light source is proposed (refer to Japanese Unexamined Patent Application Publication No. 5-232012, Japanese Unexamined Patent Application Publication No. 9-178645, Japanese Unexamined Patent Application Publication No. 2009-53020, and Japanese Unexamined Patent Application Publication No. 2005-172465). For example, in an apparatus disclosed in Japanese Unexamined Patent Application Publication No. 5-232012, a single-mode oscillation type semiconductor laser is used as a light source, laser current is controlled so as to stabilize an output of a light amount sensor built in the laser, and a preset temperature in temperature control of the laser is switched when mode hop is detected.

In an apparatus disclosed in Japanese Unexamined Patent Application Publication No. 9-178645, a laser diode which is a light source is driven by a laser driving circuit which outputs driving current obtained by superimposing a high-frequency component on direct current, so as to turn a longitudinal mode of the laser diode to multimode. In an apparatus disclosed in Japanese Unexamined Patent Application Publication No. 2009-53020, amplitude of a high-frequency wave outputted from a high-frequency wave superimposing circuit is controlled depending on intensity of direct current which is outputted from a direct current driving circuit, so as to multimode-oscillate a laser diode. Further, in an apparatus disclosed in Japanese Unexamined Patent Application Publication No. 2005-172465, a high-frequency current component from an oscillator is superimposed on driving current of a semiconductor laser so as to make an oscillation central wavelength of the semiconductor laser follow a resonance wavelength.

SUMMARY

In a fine particle analyzing apparatus such as a flow cytometer, a detection signal largely varies due to displacement of an irradiation spot of excitation light (laser beam). Therefore, it is necessary to constantly maintain the position of the irradiation spot steady so as to stabilize performance of the apparatus and enhance measurement accuracy. However, even though it is necessary to strictly manage spot position displacement of excitation light in a case where a single mode fiber is used, displacement actually easily occurs due to vibration applied to the apparatus, temperature change, and the like, and there is also a case where temporal displacement occurs naturally. Especially, in a case where measurement is performed by using a microchip, optical axis adjustment has to be performed whenever chips are exchanged. Further, positional accuracy of a flow path which is formed in a chip and accuracy in attaching a chip to the apparatus exert influence, so that a detection signal is deteriorated disadvantageously when adjustment is not properly performed.

On the other hand, when laser driving is controlled as the apparatuses disclosed in Japanese Unexamined Patent Application Publication No. 5-232012, Japanese Unexamined Patent Application Publication No. 9-178645, Japanese Unexamined Patent Application Publication No. 2009-53020, and Japanese Unexamined Patent Application Publication No. 2005-172465, the light amount of an irradiation spot and the like can be stabilized. However, these techniques of the related art are premised on the use of a single mode fiber. Therefore, if these techniques are applied to a top-hat fiber, profiles of beam intensity are not uniform in a spot and speckles are generated, deteriorating a signal-to-noise ratio (S/N ratio) of a detection signal depending on a position of a spot and a position of a flow path through which cells flow.

It is desirable to provide a fine particle analyzing apparatus and a fine particle analyzing method in which less noise caused by a light source occurs and highly-accurate measurement can be stably performed in measurement using a microchip.

A fine particle analyzing apparatus according to an embodiment of the present application includes a light irradiation unit configured to irradiate a fine particle that flows in a flow path with a laser beam, and a detection unit configured to detect light emitted from the fine particle that is irradiated with the laser beam. In the fine particle analyzing apparatus, the light irradiation unit includes at least a light source that is composed of a semiconductor laser, an optical fiber that converts a beam pattern of the laser beam generated from the light source into a top-hat type beam pattern, and a light source driving control unit configured to supply driving current, which is obtained by superimposing high-frequency current on direct current, to the light source.

In the apparatus, the light source driving control unit may include at least a high-frequency oscillator, a broadband amplifier, and a current switching circuit, and the high-frequency oscillator, the broadband amplifier, and the current switching circuit may be coupled in a direct current way.

In this case, the current switching circuit may be an emitter-coupled circuit and may adjust superimposed current based on average current taken out from an output terminal that is not connected with the light source.

Further, a sectional shape of a core on an output end side of the optical fiber may be one of a rectangular shape and an approximate rectangular shape.

A fine particle analyzing method according to another embodiment of the present application includes, after making a laser beam emitted from a light source that is composed of a semiconductor laser incident on an optical fiber and converting a beam pattern of the laser beam into a top-hat type beam pattern by the optical fiber, irradiating a fine particle that flows in a flow path with the converted laser beam, and detecting light emitted from the fine particle that is irradiated with the laser beam. In the fine particle analyzing method, driving current that is obtained by superimposing high-frequency current on direct current is supplied to the light source.

According to the embodiments of the present application, excitation light is radiated via a top-hat fiber and large-amplitude high-frequency current is superimposed on driving current of a semiconductor laser which is a light source, so that less noise caused by the light source is generated and highly-accurate measurement can be stably performed in measurement using a microchip.

Additional features and advantages are described herein, and will be apparent from the following Detailed Description and the figures.

BRIEF DESCRIPTION OF THE FIGURES

FIGS. 4A to 4E illustrate an operation of a high-frequency driving circuit depicted in FIG. 3.

DETAILED DESCRIPTION

An embodiment of the present application is described in detail below with reference to the accompanying drawings. It should be noted that the present application is not limited to the embodiment described below. The description is given in the following order.
1. Embodiment
(Example of Fine Particle Analyzing Apparatus Provided with Light Source Driving Control Unit)
2. Modification of Embodiment
(Example of Fine Particle Analyzing Apparatus Provided with Acoustooptic Element as well as Light Source Driving Control Unit)
<1. Embodiment>
[Whole Configuration of Fine Particle Analyzing Apparatus]

Figure 1:
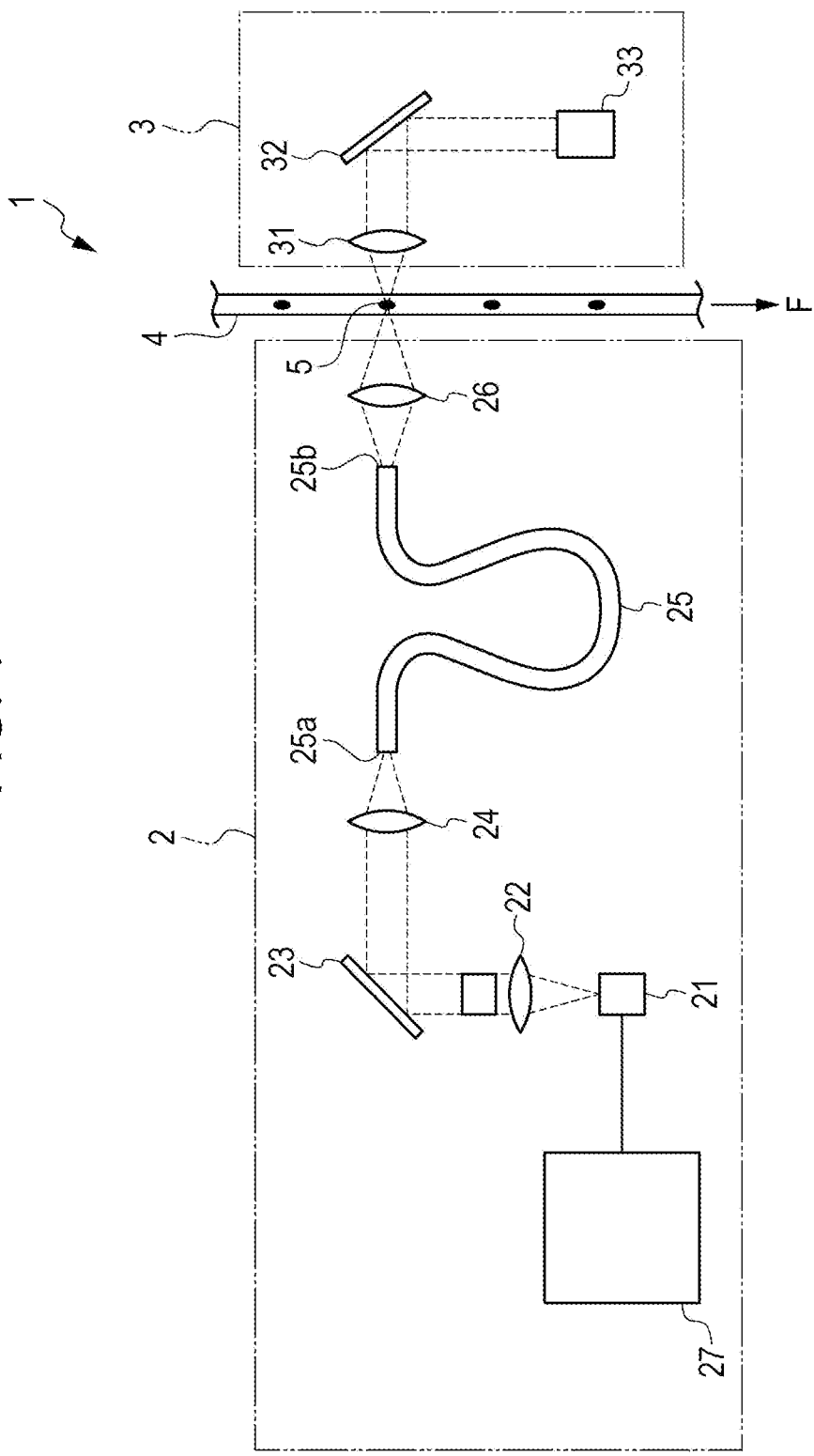
FIG. 1 schematically illustrates the configuration of a fine particle analyzing apparatus according to an embodiment of the present application.

The configuration of a fine particle analyzing apparatus according to an embodiment of the present application is described first. FIG. 1 schematically illustrates the configuration of the fine particle analyzing apparatus according to the embodiment of the present application. As depicted in FIG. 1, a fine particle analyzing apparatus 1 of the embodiment includes a light irradiation unit 2 which irradiates fine particles 5, which flow inside a sample flow 4 in a line, with laser beams and a detection unit 3 which detects fluorescence and/or scattering light emitted from the fine particles 5 which are irradiated with laser beams.
[Light Irradiation Unit 2]

The light irradiation unit 2 includes at least a light source 21 which generates a laser beam which is excitation light, an optical fiber 25 which converts a beam pattern of the laser beam emitted from the light source 21 into a top-hat type beam pattern, and a light source driving control unit 27 which controls driving of the light source 21. The light irradiation unit 2 may further include a collimator lens 22, a mirror 23, and condenser lenses 24 and 26 as necessary.

Figure 2A:
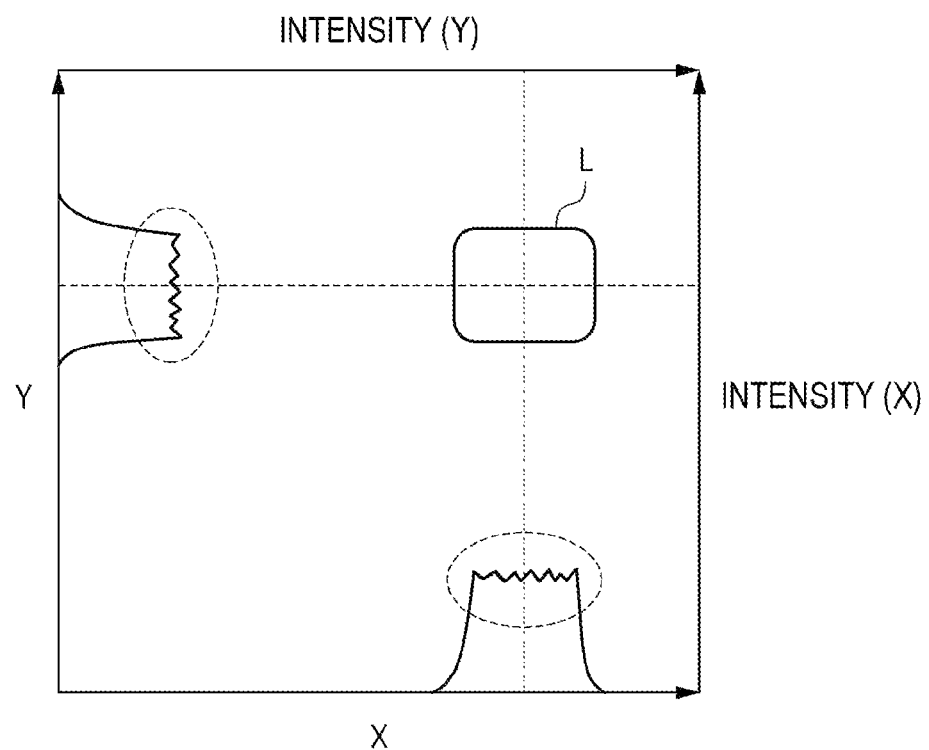
FIG. 2A illustrates beam intensity of a laser beam emitted from a top-hat type optical fiber.
Figure 2B:
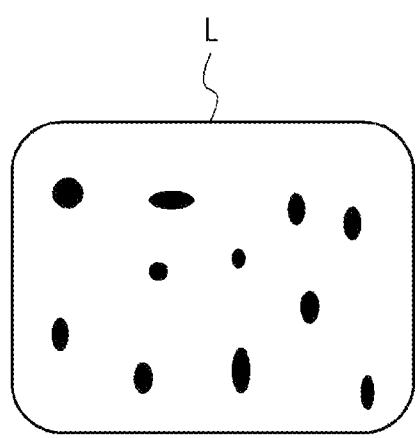
FIG. 2B illustrates a beam spot shape of the laser beam.

FIG. 2A illustrates beam intensity of a laser beam emitted from the top-hat type optical fiber 25, and FIG. 2B illustrates a beam spot shape of the laser beam. A laser beam incident from an incident end 25a of the top-hat type optical fiber 25 propagates in a core in a manner to be separated into many modes and travels in a manner to expand in the core so as to be emitted from an output end 25b in a state that the laser beam is evenly expanded in the whole region of the core.

Then, the laser beam passes through the top-hat type optical fiber 25, and sectional intensity of the excitation light (laser beam) radiated to the sample flow 4 is distributed approximately evenly in a manner to have a shape (output spot L) corresponding to the core shape at the output end 25b, as depicted in FIG. 2A. Here, it is preferable that the core shape at the output end 25b of the top-hat type optical fiber 25 be a rectangular shape or a shape close to a rectangular shape (referred to below as an approximate rectangular shape). Accordingly, even if flowing positions of the fine particles fluctuate, the laser beam can be evenly radiated.

On the other hand, even when the top-hat type optical fiber 25 is used, there is a case where a beam may not have a top-hat shape due to a speckle of a near-field pattern (NFP) or fluctuation of the light source 21 caused by mode hop may occur (refer to parts surrounded by a dashed line in FIG. 2A). Pass of the fine particles through regions (blacked out parts in FIG. 2B) in which beam intensity is small in the output spot L causes degradation of detecting accuracy.

Figure 3:
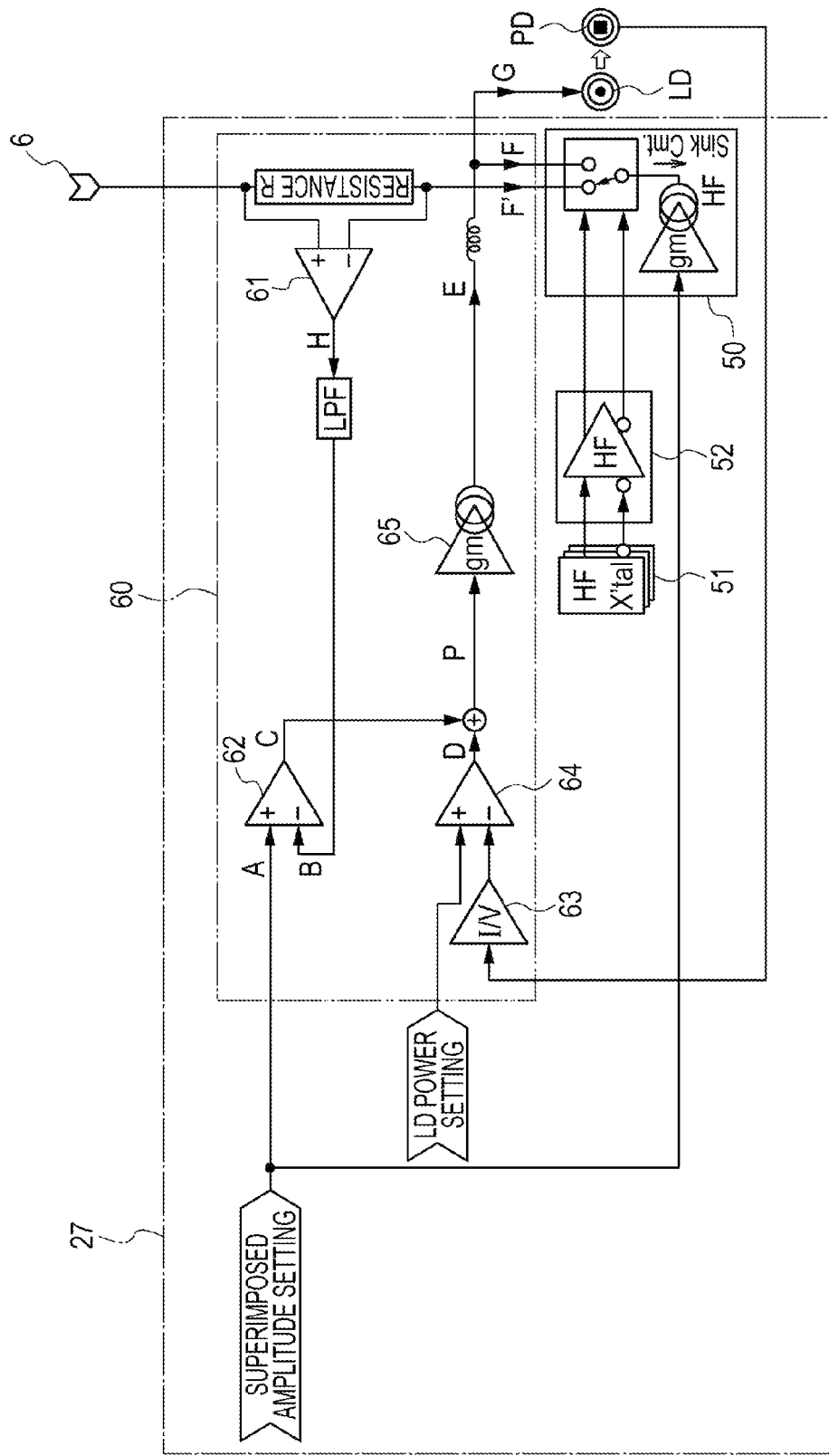
FIG. 3 illustrates the configuration of a light source driving control unit.

Therefore, in the fine particle analyzing apparatus 1 of the embodiment, a semiconductor laser (laser diode) is used as the light source 21 and driving of the laser diode is controlled by the light source driving control unit 27. FIG. 3 illustrates the configuration of the light source driving control unit 27. FIGS. 4A to 4E illustrate an operation of a high-frequency driving circuit 50 depicted in FIG. 3. Here, FIG. 3 illustrates an example in which a laser diode LD is used as the light source 21 and a photo diode PD is used as a detector 33.

The light source driving control unit 27 supplies driving current which is obtained by superimposing large-amplitude high-frequency current on direct current to the laser diode LD which is the light source 21, and includes at least a high-frequency oscillator (superimposed signal oscillating circuit 51), a broadband amplifier (high-frequency amplifier circuit 52), and a current switching circuit (high-frequency driving circuit 50). The superimposed signal oscillating circuit 51, the high-frequency amplifier circuit 52, and the high-frequency driving circuit 50 are coupled in a direct current way.

The high-frequency driving circuit 50 drives the laser diode LD which is the light source 21 and is provided close to the laser diode LD. For example, the high-frequency driving circuit 50 may have the configuration of an emitter-coupled current switching circuit. However, if the laser diode LD is driven by the circuit configuration of the current switching circuit, an average current value of current flowing to the laser diode LD varies depending on ON and OFF of superimposition. That is, a common emitter-coupled current switching circuit employs a system in which pulse-shaped current is subtracted from direct current which is supplied via an auto power control (APC) and the like, so that average current decreases according to a pulse shape.

Therefore, it is necessary to compensate reduced current. However, in a case where reduced current is compensated by the APC, the APC automatically raises the average current when superimposed amplitude is raised. Therefore, the average current hardly falls below threshold current of the laser diode LD. As a result, efficiency of high-frequency superimposition is lowered, and further, efficiency may wear off.

Therefore, the fine particle analyzing apparatus 1 according to the embodiment employs the configuration in which average current does not vary even if superimposition is applied. In particular, in the high-frequency driving circuit 50, one output terminal of the current switching circuit is connected with the laser diode LD and the other output terminal is connected to the outside so as to take out current, which is not supplied to the laser diode LD, to the outside. Calculation is performed with taken-out average current and preset amplitude and further, direct current C is added to control current D from the APC 60. Accordingly, the average current flowing to the laser diode LD can be made constant irrespective of ON/OFF of high-frequency superimposition.

The APC 60 in the light source driving control unit 27 is composed of subtraction circuits 61 and 62, a current voltage conversion circuit 63, a differential amplifier circuit 64, a voltage current conversion circuit 65, and the like, for example, and is connected with a power source 6.

Further, the high-frequency driving circuit 50 is disposed close to the laser diode LD (within several mm), but the high-frequency driving circuit 50 may be disposed apart (several dozen cm) from the laser diode LD because the direct current C which is one direct current can be added to the control current D from the APC 60 to drive the high-frequency driving circuit 50. However, in this case, it is preferable that alternating separation should be performed by a coil before the high-frequency current and the direct current are mixed.

FIGS. 4A to 4E illustrate an operation of the high-frequency driving circuit 50 depicted in FIG. 3. When amplitude A of superimposition is set as depicted in FIG. 4D, an average of superimposed current, that is, an output of a current switch which is not connected with the laser diode LD is detected as depicted in FIG. 4E. As depicted in FIG. 4A, when this value is set to be B, direct current to be added is C. Then, as depicted in FIG. 4B, this C is added to the control current D (direct current) from the APC 60 so as to be applied to the laser diode LD.

Accordingly, as depicted in FIG. 4C, current obtained by subtracting switching current G from direct current of C+D flows to the laser diode LD. Accordingly, a current average value to the laser diode LD is expressed as $(D \times gm - k \times gm \times A) + k \times gm \times A = D \times gm$. Thus, the average current flowing to the laser diode LD agrees. Here, a dimension from FIG. 4B to FIG. 4C in the vertical axis direction of FIGS. 4B and 4C is expressed by a relationship of multiplying gm, that is, $P \times gm = E$. Here, gm is an intrinsic coefficient of an amplifier which converts voltage into current.

By supplying driving current which is obtained by superimposing high-frequency current on direct current to the light source 21 by the above-described method, speckles of laser beams emitted from the output end 25b of the top-hat type optical fiber 25 can be reduced and power fluctuation of the light source 21 due to mode hop can be suppressed.

Here, in the light source driving control unit 27, a result detected by the photo diode PD may be fed back to the APC circuit.

[Detection Unit 3]

The detection unit 3 includes the optical detector 33 such as a charge coupled device (CCD) and a photo-multiplier tube (PMT), an objective lens 31, a wavelength filter 32, and the like, for example. Fluorescence and/or scattering light emitted from the fine particles 5 are/is converged at the objective lens 31 and then only a wavelength of a detection object is reflected by the wavelength filter 32 so as to be incident on the optical detector 33.

[Operation]

An operation of the fine particle analyzing apparatus 1, that is, a method for analyzing fine particles by using the fine particle analyzing apparatus 1 of the embodiment is now described. The "fine particles" measured by the fine particle analyzing method of the embodiment widely include physiologically-related fine particles such as cells, microorganisms, and ribosome, synthetic particles such as latex particles, gel particles, and industrial particles, and the like.

The physiologically-related fine particles include a chromosome, ribosome, a mitochondrion, organelle, and the like which constitute various cells. Further, cells include plant cells, animal cells, blood cells, and the like. Further, microorganisms include bacterium such as a coli bacterium, viruses such as a tobacco mosaic virus, fungi such as a yeast cell, and the like. The physiologically-related fine particles may also include a physiologically-related polymer such as nucleic acid, protein, and a complex of nucleic acid and protein.

On the other hand, examples of industrial particles include particles composed of organic polymeric materials, inorganic materials, or metallic materials. As organic polymeric materials, polystyrene, styrene-divinylbenzen, polymethyl methacrylate, and the like may be used. As inorganic materials, glass, silica, magnetic materials, and the like may be used. As metallic materials, gold colloid, aluminum, and the like, for example, may be used. These fine particles commonly have a spherical shape but may have a non-spherical shape. In addition, a size, mass, and the like are not especially limited.

In the fine particle analyzing apparatus 1 according to the embodiment, laser beams emitted from the light source 21 of the light irradiation unit 2 are radiated to the fine particles 5 flowing in the flow path which is formed in a microchip (not depicted), via the top-hat type optical fiber 25. Then, after fluorescence and/or scattering light emitted from the fine particles 5 are acquired by the objective lens 31 of the detection unit 3, a disturbance component other than light emitted from the sample is removed by the wavelength filter 32 so as to detect the light by the optical detector 33.

At this time, the light source driving control unit 27 superimposes large-amplitude high-frequency current on direct current and supplies the superimposed current as driving current to the laser diode LD which is the light source 21. In particular, the high-frequency driving circuit 50 provided to the light source driving control unit 27 generates pulse-shaped sink current and repeatedly performs an operation "to reduce" or "not to reduce" direct current which flows to the laser diode LD. Here, the "large-amplitude high-frequency current" is current of which amplitude is equal to or more than 100 mAp-p.

As described above, in the fine particle analyzing apparatus 1 of the embodiment, laser beams emitted from the light source 21 are radiated to the fine particles 5 via the top-hat type optical fiber 25, so that sectional intensity of excitation light (laser beams) can be uniformed. Further, since the light source driving control unit 27 turns a wavelength spectrum of the laser diode LD to a multimode wavelength spectrum by high-frequency superimposition, a speckle of a NFP emitted from an output end surface of the optical fiber can be suppressed and suppression of power fluctuation, which is caused by mode hop, of the laser diode LD which is the light source can be expected.

Further, in the fine particle analyzing apparatus 1 of the embodiment, the high-frequency driving circuit 50 is driven by current and thus superimposed current is hardly fluctuated by temperature change of differential resistance of laser. Further, pulse driving is employed so as to maintain time and an interval (duty) during which the average current falls below threshold current of the laser diode LD constituting the light source 21 irrespective of amplitude of high-frequency superimposed current. Furthermore, energizing voltage of the laser diode LD and the direct current C for the APC and superimposition are used as power source voltage on the laser diode LD driving side in the high-frequency driving circuit 50.

As a result, noise caused by the light source can be reduced and highly-accurate and stable measurement can be performed even in measurement using a microchip. Accordingly, not only a difficulty level of optical axis adjustment but also positional accuracy of a flow path which is formed in a chip and accuracy of attaching the chip to the apparatus are mitigated. Therefore, loads of a worker can be reduced and measurement stability (credibility) can be enhanced.

<2. Modification of Embodiment>

Figure 5:
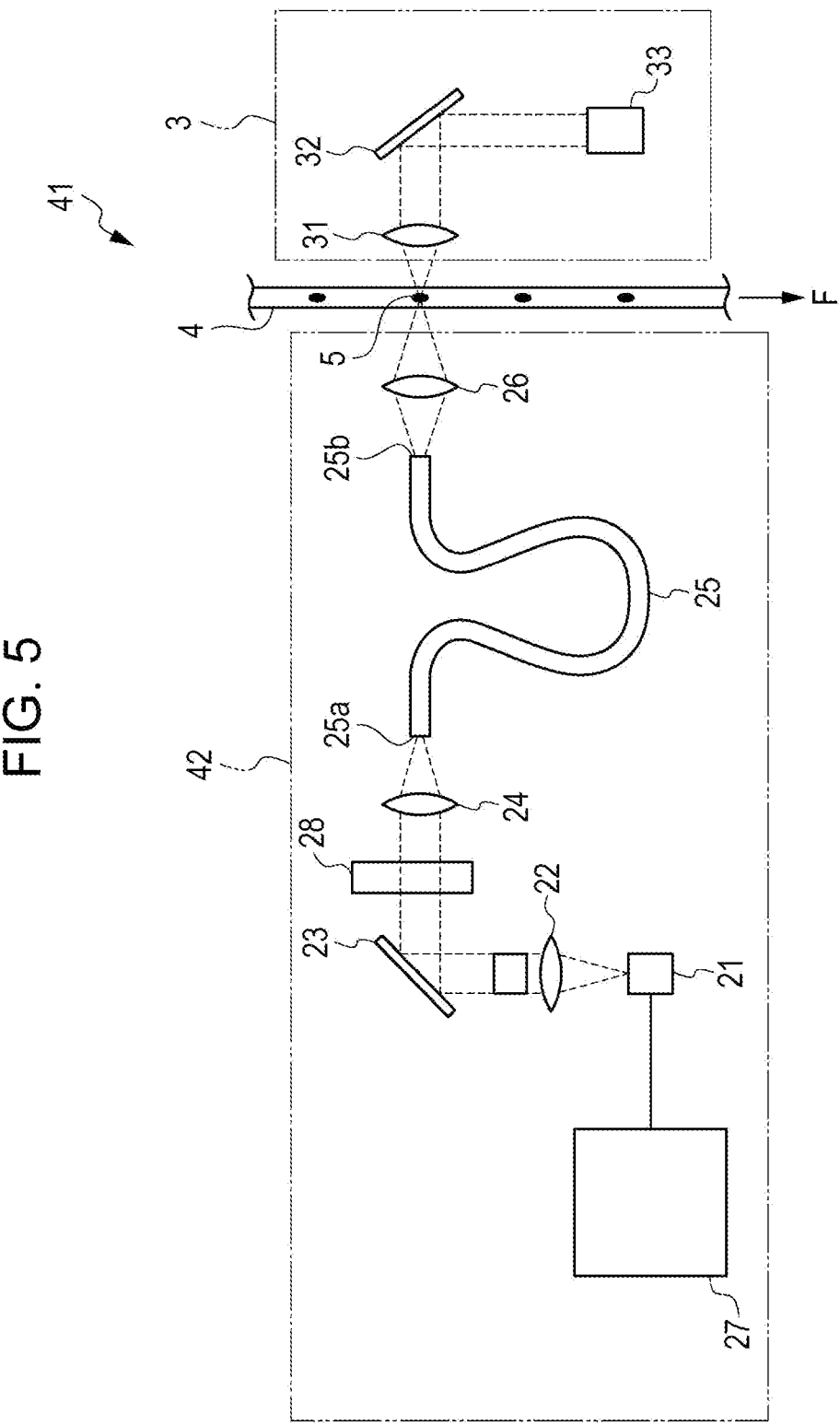
FIG. 5 schematically illustrates the configuration of a fine particle analyzing apparatus according to a modification of the embodiment of the present application.

The fine particle analyzing apparatus of the embodiment of the present application is not limited to the configuration depicted in FIG. 1. It is sufficient that a light irradiation unit includes at least a light source, a top-hat type optical fiber, and a light source driving control unit. FIG. 5 schematically illustrates the configuration of a fine particle analyzing apparatus according to a modification of the embodiment of the present application.

For example, as a fine particle analyzing apparatus 41, which is depicted in FIG. 5, of the modification of the embodiment of the present application, an acoustooptical element (AOM) 28 which changes frequency of light by using diffraction of a compression wave of crystal may be provided to a light irradiation unit 42. In this case, the acoustooptical element 28 is disposed between the light source 21 and the top-hat type optical fiber 25. The beam intensity in the output spot can be further uniformed by using the acoustooptical element 28 in combination. That is, efficiency obtained by turning a beam pattern of laser beams to a top-hat type beam pattern by the top-hat type optical fiber 25 can be further enhanced by combining the acoustooptical element 28.

Embodiments of the present application may have the following configuration.

(1) A fine particle analyzing apparatus includes a light irradiation unit configured to irradiate a fine particle that flows in a flow path with a laser beam, and a detection unit configured to detect light emitted from the fine particle that is irradiated with the laser beam. In the fine particle analyzing apparatus, the light irradiation unit includes at least a light source that is composed of a semiconductor laser, an optical fiber that converts a beam pattern of the laser beam generated from the light source into a top-hat type beam pattern, and a light source driving control unit configured to supply driving current, which is obtained by superimposing high-frequency current on direct current, to the light source.

(2) In the fine particle analyzing apparatus according to (1), the light source driving control unit includes at least a high-frequency oscillator, a broadband amplifier, and a current switching circuit, and the high-frequency oscillator, the broadband amplifier, and the current switching circuit are coupled in a direct current way.

(3) In the fine particle analyzing apparatus according to (2), the current switching circuit is an emitter-coupled circuit and adjusts superimposed current based on average current taken out from an output terminal that is not connected with the light source.

(4) In the fine particle analyzing apparatus according to any of (1) to (3), a sectional shape of a core on an output end side of the optical fiber is one of a rectangular shape and an approximate rectangular shape.

(5) A fine particle analyzing method includes, after making a laser beam emitted from a light source that is composed of a semiconductor laser incident on an optical fiber and converting a beam pattern of the laser beam into a top-hat type beam pattern by the optical fiber, irradiating a fine particle that flows in a flow path with the converted laser beam, and detecting light emitted from the fine particle that is irradiated with the laser beam. In the fine particle analyzing method, driving current that is obtained by superimposing high-frequency current on direct current is supplied to the light source.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A fine particle analyzing apparatus, comprising:
a light irradiation unit configured to irradiate a fine particle that flows in a flow path with a laser beam; and
a detection unit configured to detect light emitted from the fine particle that is irradiated with the laser beam; wherein
the light irradiation unit includes at least
a light source that is composed of a semiconductor laser,
an optical fiber that converts a beam pattern of the laser beam generated from the light source into a top-hat type beam pattern, and
a light source driving control unit configured to supply driving current, the driving current being obtained by superimposing high-frequency current on direct current, to the light source;
wherein the light source driving control unit includes at least a high-frequency oscillator, a broadband amplifier, and a current switching circuit, and the high-frequency oscillator, the broadband amplifier, and the current switching circuit are coupled in a direct current way.

2. The fine particle analyzing apparatus according to claim 1, wherein the current switching circuit is an emitter-coupled circuit and adjusts superimposed current based on average current taken out from an output terminal that is not connected with the light source.

3. The fine particle analyzing apparatus according to claim 1, wherein a sectional shape of a core on an output end side of the optical fiber is one of a rectangular shape and an approximate rectangular shape.

4. A fine particle analyzing method, comprising:
after making a laser beam emitted from a light source that is composed of a semiconductor laser incident on an optical fiber and converting a beam pattern of the laser beam into a top-hat type beam pattern by the optical fiber, irradiating a fine particle that flows in a flow path with the converted laser beam; and
detecting light emitted from the fine particle that is irradiated with the laser beam; wherein
driving current, via a light source driving control unit, that is obtained by superimposing high-frequency current on direct current is supplied to the light source;
wherein the light source driving control unit includes at least a high-frequency oscillator, a broadband amplifier, and a current switching circuit, and the high-frequency oscillator, the broadband amplifier, and the current switching circuit are coupled in a direct current way.

* * * * *